United States Patent [19]
De Lange

[11] Patent Number: 5,733,730
[45] Date of Patent: Mar. 31, 1998

[54] TELOMERE REPEAT BINDING FACTOR AND DIAGNOSTIC AND THERAPEUTIC USE THEREOF

[75] Inventor: Titia De Lange, New York, N.Y.

[73] Assignee: The Rockefeller University, New York, N.Y.

[21] Appl. No.: 519,103

[22] Filed: Aug. 25, 1995

[51] Int. Cl.⁶ .............................. C12Q 1/68; G01N 33/53
[52] U.S. Cl. .................................................. 435/6; 435/7.1
[58] Field of Search ........................ 435/6, 7.1, 7.7; 530/350

[56] References Cited

PUBLICATIONS

Allshire et al (1988) Nature 332:656–659;.
Blackburn et al (1984) Cell 36:447–458;.
Broccoli et al. (1995) Proc. Natl. Acad. Sci. USA 92:9082–6.
Brown (1986) Nature 338:774–776; Cross et al (1989) Nature 338:771–774.
Cardenas et al in 1993 (Genes and Devel. 7:883–894).
Chong et al. (1995) Science 270, 1663–1667.
Cross et al (1989) Nature 338:771–774.
DePalma, A. (1995) Genet. Engin. News 15(16):1,13.
Hanish et al (1994) Proc. Natl. Acad. Sci. USA 91:8861–8865.
Ishikawa et al (1993) Mol. Cell Biol. 13:4301–4310;.
de Lange, T. (1995) "Telomere Dynamics and Genome Instability in Human Cancer," in Telomeres, Cold Spring Harbor Monograph, E. H. Blackburn and C. W. Greider, Eds.
de Lange Proc. Natl. Acad. Sci. USA 91:2882–2885, 1994.
de Lange (EMBO J. 11:717–724, 1992).
de Lange et al (Mol. Cell. Biol. 10:518–527, 1990.
Lundblad et al (1989) Cell 83:633–643;.
McKay et al (1992) Nucl. Acids Res. 20:6461–6464.
McKay et al (1992) Nucl. Acids Res. 20:1387–1391;.
Moyzis et al (1988) Proc. Natl. Acad. Sci. USA 85:6622–6626;.
Van der Ploeg et al (1984) Cell 36:459–468.
Saltman et al (1993) Chromosoma 102:121–128.
Szostak et al (1982) Cell 36:459–568.
Tommerup et al (1994) Mol. Cell Biol. 14:5777–5785.
Zakian, V.A. (1995) Science 270:1601–7.
Zhong et al (1992) Mol. Cell. Biol. 13:4834–4943.
Uhlem (Nature 340: 733–734 (1989)).
Brigati et al Mol. Cell. Biol 13:1306–1314 (1993).

Primary Examiner—Eggerton A. Campbell
Attorney, Agent, or Firm—Klauber & Jackson

[57] ABSTRACT

The present invention relates to a novel nucleotide sequence encoding a telomeric protein which binds a repeat region of telomeric sequences, and to the protein encoded thereby. Also included within the invention are expression vectors for the production of the telomeric protein and host cells transformed with the nucleotide sequence. In addition, antibodies, probes and antagonists specific for the telomeric protein are contemplated. Methods of identifying antagonists of the telomeric protein, diagnostic methods of identifying the telomeric protein in a sample, and therapeutic uses of the telomeric protein, particularly in the treatment of aging and cancer, are also contemplated.

19 Claims, 9 Drawing Sheets

| T7 | E A E E V F E ... | (SEQ ID NO:1) |
| | m/z=1009.2 assuming Glu @ 4 and Arg @ C-t [MH⁺]=1009.06 Δ=0.14 dalton | |
| T8 | T L D A (Q) F E N (d) E ... | (SEQ ID NO:2) |
| | m/z=1337.9 assuming sequence as written and Arg @ C-t [MH⁺]=1338.38 Δ=0.48 dalton | |
| T10 | T I T (S) Q D K P x x N x V x M ... | (m/z=2676) (SEQ ID NO:3) |
| T11 | I L L x Y K II | (no mass) (SEM(SEQ ID NO:4) |
| T12 | N (q) A I A V ... | (m/z=1659) (SEQ ID NO:5) |
| T13 | I F (G) D P N ... | (m/z=1409) (SEQ ID NO:6) |
| T14 | N L F L ... | (no mass) (SEQ ID NO:7) |
| T20 | x Y V N Y V L x E K II | (SEQ ID NO:8) |
| | m/z=1156.6, 1172.9, 1201.4 (three signals) Assuming (x, x) = (Gly, Ala): [MH⁺]=1156.33 Assuming (x, x) = (Gly, Ser): [MH⁺]=1172.33 Assuming (x, x) = (Ser, Ser): [MH⁺]=1202.35 The "Ala" scenario is somewhat unlikely as this residue is easily detectable whereas Gly and Ser are not (at the femtomole level). | |
| T26 | Q A x L x E E D K II | (SEQ ID NO:9) |
| | no conclusive mass result was obtained the peptide contains Trp (Asp/Q??? = 25%) | |
| T29 | T I Y I C Q F L T ... | (SEQ ID NO:10) |
| | m/z=1363.0 assuming Arg @ C-t: [MH⁺]=1363.53 Δ=0.53 dalton | |

Symbols:
1) x : no residue could be identified at this position
(AMINO ACID) : identification with lower degree of confidence
(amino acid) : residue present but at very low levels 2) II indicates C-terminus of peptide
... : no more interpretable signals, but unlikely to be C-terminus 3) [M+H⁺] : sum of the average isotopic masses of all identified (positively and tentatively) residues plus one proton (H⁺)
m/z : experimental mass (by laser-desorption mass spectrometry)

FIG.1A

T7: E A E E V F E . . .  (SEQ ID NO:1)
            t m/z=1009.2
assuming Glu @ 4 and Arg @ C-t: [MH+]=1009.06
Δ=0.14 dalton T8: T L D A (Q) F E N (d) E . . .  (SEQ ID NO:2)

m/z=1337.9
assuming sequence as written and Arg @ C-t: [MH+]=1338.38
Δ=0.48 dalton T10: T I T (S) Q D K P x x N x V x M . . .  (m/z=2676)  (SEQ ID NO:3)

T11: I L L x Y K ‖  (no mass)  (SEW(SEQ ID NO:4)

T12: N (q) A I A V . . .  (m/z=1659)  (SEQ ID NO:5)

T13: I F (G) D P N . . .  (m/z=1409)  (SEQ ID NO:6)

T14: N L F L . . .  (no mass)  (SEQ ID NO:7)

T20: x Y V N Y V L x E K ‖  (SEQ ID NO:8)

FIG. 1B m/z=1156.6, 1172.9, 1201.4 (three signals)
Assuming (x, x) = (Gly, Ala) : [MH⁺]=1156.33
Assuming (x, x) = (Gly, Ser) : [MH⁺]=1172.33
Assuming (x, x) = (Ser, Ser) : [MH⁺]=1202.35

The "Ala" scenario is somewhat unlikely as this residue is easily detectable whereas Gly and Ser are not (at the femtomole level).

T26:      Q A x L x E E D K ‖      (SEQ ID NO:9)

no conclusive mass result was obtained
the peptide contains Trp ($A_{297/277}$ = 25%)

T29:      T I Y I C Q F L T . . .      (SEQ ID NO:10)

m/z=1363.0
assuming Arg @ C-t: [MH⁺]=1363.53
Δ=0.53 dalton

Symbols:
1) x : no residue could be identified at this position
(AMINO ACID) : identification with lower degree of confidence
(amino acid) : residue present but at very low levels 2) ‖ indicates C-terminus of peptide
. . . : no more interpretable signals, but unlikely to be C-terminus 3) [M+H⁺] : sum of the average isotopic masses of all identified (positively and tentatively) residues plus one proton [H⁺]
m/z : experimental mass (by laser-desorption mass spectrometry)

FIG.2A

Sequence Range: 1 to 1629

```
                  *         *         *         *         *
         ATCGAGCCAT TTAACATGGC GGAGGATGTT TCCTCAGCGG CCCCGAGCCC  50
                  *         *         *         *         *
         CGGGGGGTGT GGGGATGGTA GGGATGCCGA CCCTACTGAG GAGCAGATGG  100
          I E P P N|M A  E D V  S S A  A P S P  R R C  A D G  R D A D  P T E  E Q M>
               START
                  *         *         *         *         *
         CAGAAACAGA GAGAACGACG GAGGAGCAGT TGAATGCCAG CAGTTGTCTC GAGTTGCAGG  150
                                                              XnoI
                                                           GAGTTGCAGG  200
          A E T E  R N D  G G A S  E C Q  P E C Q  E L L  E  C Q
                  *         *         *         *         *
         TGAACTGCTG TGCCTGCAGG TGGGGAAGAGG GCCCCCCGAG AGGAGGAGGA  300
          V Q V G  A P E  E E E E>
                  *         *         *         *         *
         GGACCTGCCC CTGGTCGCCG AGGCCGAGGC GGCTGAGGCC CTTGCCGAG CTTCCGGA CGGCCCTC  400
          D A G  L V A  E A E A  A A E A  L C R  A F R D  G R S>
                  *         *         *         *         *
         GAGGACTTCC GCAGGACGCC CAACAGCGCA GAGGTATTTA TTCATGGACT ATCCAGTGCT ACAGAGAAC GATATACATA TGTCAGTTTT  500
          E D F  R R T R  N S A  E A I  I H G L  S S L  T A C  Q L R T  I Y I  C Q F>
                  *         *         *         *         *
         TGACAAGAT TGCAGCAGGA AAAACCCTTG ATGCACAGTT TGAAAATGAT GAAGGAATTA CAGAATTC CACCCTTGA GTGTTGTATC GAAGAATGGA ATCGCCTGG ATGATTTGG GTTCAATTGA  600
          L T R I  A A G  K T L  D A Q P  E N D  E R I T  P L E S A L  M I W  G S I E>
                  *         *         *         *         *
         AAAGGAACAT GACAAACTTC ATGAAGAAAT ACAGAATTA ATTAAAATTC AGGCTATAGC CAAATTGCTT CTTCAAAAG ATGATAAATC GAAAAATGGC GAAAATGGCA CTCAGAAAGA AGGAGAAGA  700
          K E H D K L  H E E I Q N L  I K I  Q A I A  K L L  M I I  S Q K D  E N G  N P K E  A E E>
                  *         *         *         *         *
         GTCTTTGAAA GAATATTTGG TGATCCAAAT TCTCATATGT CCCTTCAAAG ATGATAAATC CTTCAAAAG CTTCAAAAG GTGAAAAATC TACATTCAT TCTTTTTTC  800
          V F E  R I F G  D P N  S H M  P F K S  K L L  M I I  S Q K D  T F H  S P F>
                  *         *         *         *         *
         AACACTTCAG CTTACAACAG ATGATGGAGA AAATTAAGAG TATGTGCTAA TATGTGAAT GTGAAAAATC CTAATGAAGG CAGGGCAAA
          Q H P S  Y N H M M E  K I K S  Y V N  Y V L  S E K S  S T P  L M K  A A A K>
```

FIG. 2B

```
                                                                              900
                                                           850                 *
AGTAGTAGAA AGCAAAAGGA CAAGACAAT AACTTCTCAA GATAAACCTA GTGGTAATGA TGTTGAAATG GAAACTGAAG CTAATTTGGA TACAAGAAAA
 V  V  E   S  K  R    T  R  T  I  T  S  Q   D  K  P    S  G  N  D  V  E  M   E  T  E    A  N  L  D  T  R  K>
                                                                              1000
                                    950                                        *
AGTGTTAGTG ACAAACAGTC TGCGGTAACT GAATCCTCAG AGGTACAGT ATCCTTATG AGTCTCACA AGAATCTTT CTTATCTAAG TTGCAACATG
 S  V  S   D  K  Q  S  A  V  T   E  S  S   E  G  T  V  S  L  L   R  S  H   K  N  L  P   L  S  K    L  Q  H>
                                                                              1100
                                   1050                                        *
GAACCCAGCA ACAAGACCTT AATAAGAAAG AAAGAAGAGT AGGAACTCCT CAAAGTACAA AGGAGAAAAA AGAAAGCAGA AGAGCCACTG AAAGCAGAAT
 G  T  Q  Q  D  L    N  K  K    E  R  R  V  G  T  P    Q  S  T   K  K  K    E  S  R    R  A  T    E  S  R  I>
                                                                              1200
                                   1150                                        *
ACTGTGTTCA AAGAGTCAGC CGTAACTCC TGAAAACAT CGAGCTAGAA AAAGCAGGC ATGGCTTTGG GAAGAAGACA AGAATTTGAG ATCTGGCGTG
 P  V  S   K  S  Q    P  V  T  P  E  K  H  R  A  R    K  R  Q  A  W  L  W   E  E  D    K  N  L  R  S  G  V>
                                                                              1300
                                   1250                                        *
AGGAAATATG GAGAGGGAAA CTGGTCTAAA ATACTGTTGC ATTATAAATT CAACAACCGG ACAAGTGTCA TGTTAAAAGA CAGATGAAGG ACCATGAAGA
 R  K  Y   G  E  G  N  W  S  K   I  L  L    H  Y  K  P  N  N  R   T  S  V   M  L  K  D  R  W  R    T  M  K>
                                                                              1400
                                   1350                                        *
AACTAAAACT GATTCCTCTA GACACGGAAG ACTGATGTG TTTGTAAAG CTTGATGAAA GGACAGTTAA GTATTTTGAT CACTGCATTT TGTTTGAAC
 K  L  K  L  I  S  S   D  S  E   D  * L  C  L  *  K   L  D  E   R  T  V  K  Y  F  D   H  C  I    L  F  E  T>
                               STOP                                           1500
                                                                               *
                                   1450
TTGTGTCATT GATGTAATTT AAAACTTTTG TTTAAAGCAT TACAGTATTT TTCTGTGACC ATCAATTAAT GAGGTTTGT GCTACCAGAG TTAAAGCATA
 C  V  I   D  V  I    *  N  F  C  L  K  H   Y  S  I  F  L  *  P   S  I  N   E  G  L   C  Y  Q  S    *  S  I>
                                                                              1600
                                   1550                                        *
TGCTATCATT GTATTCTTTA AGAACTTTAT TTGAATAAAA TGTAAATTTG TTGAACCCTG CCACATTTAG TATCCCGACC CCCAAATCCT GTTCCAATGA
 C  Y  H   C  I  L    *  E  P  Y  F  D  K  M  *  I  C   *  T  L  P  H  L  V  S  P  P  P  N  P    V  P  M>

AAAAATTAAA ACCTGATACG AAAAAAAAA
 K  K  L  K  P  D  T   K  K  K>
```

FIG. 3

MAEDVSSAAPSPRRCADGRDADPTEEQMAETERN*DEEQFECQELLECQVQVG*
*APEEEEEEEEDAGLVAEAEAVAAGWMLDFLCLSLCRAFRDGRSEDFRRTRNS*
AEAIIHGLSSLTACQL<u>RTIYICQFLTR</u>IAAGK<u>TLDAQFENDER</u>ITPLESALM
IWGSIEKEHDKLHEEIQNLIK<u>IQAIAV</u>CMENGNFK<u>EAEEVFERIFGDPN</u>SHM
PFKSKLLMIISQKDTFHSFFQHFSYNHMMEKIKS<u>YVNYVLSEK</u>SSTFLMKAA
AKVVESKRTR<u>TITSQDKPSGNDVEM</u>ETEANLDTRKSVSDKQSAVTESSEGTV
SLLRSHKN<u>LFL</u>SKLQHGTQQQDLNKKERRVGTPQSTKKKKESRRATESRIPV
SKSQPVTPEKHRARKRQAWLWEEDKNLRSGVRKYGEGNWSK<u>ILLHYK</u>F
NNRTSVMLKDRWRTMKKLKLISSDSED

FIG. 4

```
Hu amyb R2   LIKGPWTKEEDQRVIELVQKYGPKRWSLIAKHLKG..RIGKQCRERWHNHLNPE
Mu cmyb R2   LIKGPWTKEEDQRVIKLVQKYGPKRWSVIAKHLKG..RIGKQCRERWHNHLNPE
Hu TRF       RKRQAWLWEEDKNLRSGVRKYGEGNWSKILLHYKFNNRTSVMLKDRWR.TMKKL
Hu amyb R3   VKKSSWTEEEDRIIYEAHKRLG..NRWAEIAKLLPG..RTDNSIKNHWNSTMRRK
Hu bmyb R3   VKKSCWTEEEDRIICEAHKVLG..NRWAEIAKMLPG..RTDNAVKNHWNSTIKRK
Mu cmyb R3   VKKTSWTEEEDRIIYQAHKRLG..NRWAEIAKLLPG..RTDNAIKNHWNSTMRRK
Dro myb R3   IKKTAWTEKEDEIIYQAHLELG..NQWAKIAKRLPG..RTDNAIKNHWNSTMRRK
```

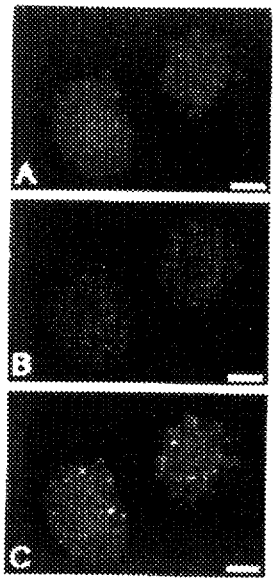
FIG.7A
FIG.7B
FIG.7C
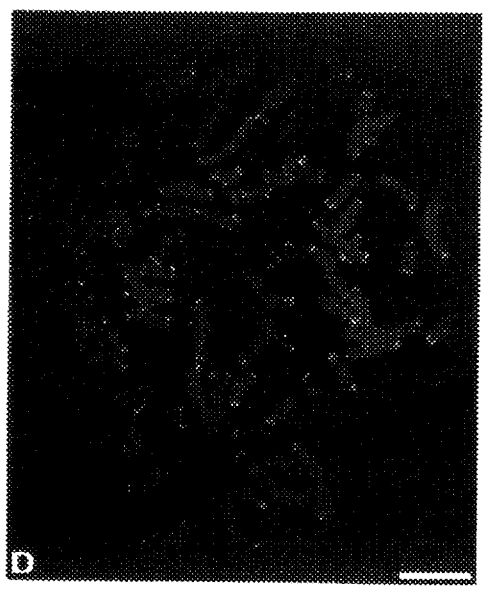
FIG.7D

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Glu  Ala  Glu  Glu  Val  Phe  Glu
    1                    5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Thr  Leu  Asp  Ala  Gln  Phe  Glu  Asn  Asp  Glu
    1                    5                         10

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Thr Ile Thr Ser Gln Asp Lys Pro Xaa Xaa Asn Xaa Val Xaa Met
1               5                   10                  15
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ile Leu Leu Xaa Tyr Lys
1               5
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Asn Gln Ala Ile Ala Val
1               5
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Ile Phe Gly Asp Pro Asn
1               5
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Asn Leu Phe Leu
1
```

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
    Xaa  Tyr  Val  Asn  Tyr  Val  Leu  Xaa  Glu  Lys
    1              5                        10
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
    Gln  Ala  Xaa  Leu  Xaa  Glu  Glu  Asp  Lys
    1              5
```

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
    Thr  Ile  Tyr  Ile  Cys  Gln  Phe  Leu  Thr
    1              5
```

( 2 ) INFORMATION FOR SEQ ID NO:11:

( i ) SEQUENCE CHARACTERISTICS:
        ( A ) LENGTH: 1629 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
ATCGAGCCAT TTAACATGGC GGAGGATGTT TCCTCAGCGG CCCCGAGCCC GCGGCGGTGT      60
GCGGATGGTA GGGATGCCGA CCCTACTGAG GAGCAGATGG CAGAAACAGA GAGAAACGAC     120
GAGGAGCAGT TCGAATGCCA GGAACTGCTC GAGTGCCAGG TGCAGGTGGG GGCCCCCGAG     180
GAGGAGGAGG AGGAGGAGGA GGACGCGGGC CTGGTGGCCG AGGCCGAGGC CGTGTGGCCG     240
GGCTGGATGC TCGATTTCCT CTGCCTCTCT CTTTGCCGAG CTTTCCGCGA CGGCCGCTCC     300
GAGGACTTCC GCAGGACCCG CAACAGCGCA GAGGCTATTA TTCATGGACT ATCCAGTCTA     360
ACAGCTTGCC AGTTGAGAAC GATATACATA TGTCAGTTTT TGACAAGAAT TGCAGCAGGA     420
AAAACCCTTG ATGCACAGTT TGAAAATGAT GAACGAATTA CACCCTTGGA ATCAGCCCTG     480
ATGATTTGGG GTTCAATTGA AAAGGAACAT GACAAACTTC ATGAAGAAAT ACAGAATTTA     540
ATTAAAATTC AGGCTATAGC TGTTTGTATG GAAAATGGCA ACTTTAAAGA AGCAGAAGAA     600
GTCTTTGAAA GAATATTTGG TGATCCAAAT TCTCATATGC CTTCAAAAG  CAAATTGCTT     660
ATGATAATCT CTCAGAAAGA TACATTTCAT TCCTTTTTTC AACACTTCAG CTACAACCAC     720
ATGATGGAGA AAATTAAGAG TTATGTGAAT TATGTGCTAA GTGAAAAATC ATCAACCTTT     780
CTAATGAAGG CAGCGGCAAA AGTAGTAGAA AGCAAAAGGA CAAGAACAAT AACTTCTCAA     840
GATAAACCTA GTGGTAATGA TGTTGAAATG GAAACTGAAG CTAATTTGGA TACAAGAAAA     900
AGTGTTAGTG ACAAACAGTC TGCGGTAACT GAATCCTCAG AGGGTACAGT ATCCTTATTG     960
```

-continued

```
AGGTCTCACA  AGAATCTTTT  CTTATCTAAG  TTGCAACATG  GAACCCAGCA  ACAAGACCTT   1020
AATAAGAAAG  AAAGAAGAGT  AGGAACTCCT  CAAAGTACAA  AAAAGAAAAA  AGAAAGCAGA   1080
AGAGCCACTG  AAAGCAGAAT  ACCTGTTTCA  AAGAGTCAGC  CGGTAACTCC  TGAAAAACAT   1140
CGAGCTAGAA  AAAGACAGGC  ATGGCTTTGG  GAAGAAGACA  AGAATTTGAG  ATCTGGCGTG   1200
AGGAAATATG  GAGAGGGAAA  CTGGTCTAAA  ATACTGTTGC  ATTATAAATT  CAACAACCGG   1260
ACAAGTGTCA  TGTTAAAAGA  CAGATGGAGG  ACCATGAAGA  AACTAAAACT  GATTCCTCA    1320
GACAGCGAAG  ACTGATTGTG  TTTGTAAAAG  CTTGATGAAA  GGACAGTTAA  GTATTTTGAT   1380
CACTGCATTT  TGTTTGAAAC  TTGTGTCATT  GATGTAATTT  AAAACTTTTG  TTTAAAGCAT   1440
TACAGTATTT  TTCTGTGACC  ATCAATTAAT  GAGGGTTTGT  GCTACCAGAG  TTAAAGCATA   1500
TGCTATCATT  GTATTCTTTA  AGAACCTTAT  TTTGATAAAA  TGTAAATTTG  TTGAACCCTC   1560
CACATTTAGT  ATCCCCACCC  CCAAATCCTG  TTCCAATGAA  AAAATTAAAA  CCTGATACGA   1620
AAAAAAAAG                                                              1629
```

( 2 ) INFORMATION FOR SEQ ID NO:12:

( i ) SEQUENCE CHARACTERISTICS:
( A ) LENGTH: 439 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:12:

```
Met Ala Glu Asp Val Ser Ser Ala Ala Pro Ser Pro Arg Arg Cys Ala
 1               5                  10                  15

Asp Gly Arg Asp Ala Asp Pro Thr Glu Glu Gln Met Ala Glu Thr Glu
                20                  25                  30

Arg Asn Asp Glu Glu Gln Phe Glu Cys Gln Glu Leu Leu Glu Cys Gln
                35                  40                  45

Val Gln Val Gly Ala Pro Glu Glu Glu Glu Glu Glu Glu Glu Asp Ala
        50                  55                  60

Gly Leu Val Ala Glu Ala Glu Ala Val Ala Ala Gly Trp Met Leu Asp
 65                  70                  75                  80

Phe Leu Cys Leu Ser Leu Cys Arg Ala Phe Arg Asp Gly Arg Ser Glu
                    85                  90                  95

Asp Phe Arg Arg Thr Arg Asn Ser Ala Glu Ala Ile Ile His Gly Leu
                100                 105                 110

Ser Ser Leu Thr Ala Cys Gln Leu Arg Thr Ile Tyr Ile Cys Gln Phe
            115                 120                 125

Leu Thr Arg Ile Ala Ala Gly Lys Thr Leu Asp Ala Gln Phe Glu Asn
        130                 135                 140

Asp Glu Arg Ile Thr Pro Leu Glu Ser Ala Leu Met Ile Trp Gly Ser
145                 150                 155                 160

Ile Glu Lys Glu His Asp Lys Leu His Glu Ile Gln Asn Leu Ile
                    165                 170                 175

Lys Ile Gln Ala Ile Ala Val Cys Met Glu Asn Gly Asn Phe Lys Glu
                180                 185                 190

Ala Glu Glu Val Phe Glu Arg Ile Phe Gly Asp Pro Asn Ser His Met
            195                 200                 205

Pro Phe Lys Ser Lys Leu Leu Met Ile Ile Ser Gln Lys Asp Thr Phe
        210                 215                 220
```

| | | | | | | | | | | | | | | |
|---|---|---|---|---|---|---|---|---|---|---|---|---|---|---|
| His<br>225 | Ser | Phe | Phe | Gln<br>230 | His | Phe | Ser | Tyr | Asn<br>235 | His | Met | Met | Glu | Lys | Ile<br>240 |
| Lys | Ser | Tyr | Val | Asn<br>245 | Tyr | Val | Leu | Ser | Glu<br>250 | Lys | Ser | Ser | Thr | Phe<br>255 | Leu |
| Met | Lys | Ala | Ala | Ala<br>260 | Lys | Val | Val | Glu<br>265 | Ser | Lys | Arg | Thr | Arg<br>270 | Thr | Ile |
| Thr | Ser | Gln | Asp<br>275 | Lys | Pro | Ser | Gly | Asn<br>280 | Asp | Val | Glu | Met<br>285 | Glu | Thr | Glu |
| Ala | Asn<br>290 | Leu | Asp | Thr | Arg | Lys<br>295 | Ser | Val | Ser | Asp | Lys<br>300 | Gln | Ser | Ala | Val |
| Thr<br>305 | Glu | Ser | Ser | Glu | Gly<br>310 | Thr | Val | Ser | Leu | Leu<br>315 | Arg | Ser | His | Lys | Asn<br>320 |
| Leu | Phe | Leu | Ser | Lys<br>325 | Leu | Gln | His | Gly | Thr<br>330 | Gln | Gln | Gln | Asp | Leu<br>335 | Asn |
| Lys | Lys | Glu | Arg<br>340 | Arg | Val | Gly | Thr | Pro<br>345 | Gln | Ser | Thr | Lys | Lys<br>350 | Lys | Lys |
| Glu | Ser | Arg<br>355 | Arg | Ala | Thr | Glu | Ser<br>360 | Arg | Ile | Pro | Val | Ser<br>365 | Lys | Ser | Gln |
| Pro | Val<br>370 | Thr | Pro | Glu | Lys | His<br>375 | Arg | Ala | Arg | Lys | Arg<br>380 | Gln | Ala | Trp | Leu |
| Trp<br>385 | Glu | Glu | Asp | Lys | Asn<br>390 | Leu | Arg | Ser | Gly | Val<br>395 | Arg | Lys | Tyr | Gly | Glu<br>400 |
| Gly | Asn | Trp | Ser | Lys<br>405 | Ile | Leu | Leu | His | Tyr<br>410 | Lys | Phe | Asn | Asn | Arg<br>415 | Thr |
| Ser | Val | Met | Leu<br>420 | Lys | Asp | Arg | Trp | Arg<br>425 | Thr | Met | Lys | Lys | Leu<br>430 | Lys | Leu |
| Ile | Ser | Ser | Asp<br>435 | Ser | Glu | Asp | | | | | | | | | |

( 2 ) INFORMATION FOR SEQ ID NO:13:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

| | | | | | | | | | | | | | | |
|---|---|---|---|---|---|---|---|---|---|---|---|---|---|---|
| Leu<br>1 | Ile | Lys | Gly | Pro<br>5 | Trp | Thr | Lys | Glu | Glu<br>10 | Asp | Gln | Arg | Val | Ile<br>15 | Glu |
| Leu | Val | Gln | Lys | Tyr<br>20 | Gly | Pro | Lys | Arg | Trp<br>25 | Ser | Leu | Ile | Ala | Lys<br>30 | His |
| Leu | Lys | Gly | Arg<br>35 | Ile | Gly | Lys | Gln | Cys<br>40 | Arg | Glu | Arg | Trp | His<br>45 | Asn | His |
| Leu | Asn | Pro | Glu<br>50 | | | | | | | | | | | | |

( 2 ) INFORMATION FOR SEQ ID NO:14:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Leu Ile Lys Gly Pro Trp Thr Lys Glu Glu Asp Gln Arg Val Ile Lys
1               5                   10                  15

Leu Val Gln Lys Tyr Gly Pro Lys Arg Trp Ser Val Ile Ala Lys His
                20                  25                  30

Leu Lys Gly Arg Ile Gly Lys Gln Cys Arg Glu Arg Trp His Asn His
            35                  40                  45

Leu Asn Pro Glu
            50
```

(2) INFORMATION FOR SEQ ID NO:15:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Arg Lys Arg Gln Ala Trp Leu Trp Glu Glu Asp Lys Asn Leu Arg Ser
1               5                   10                  15

Gly Val Arg Lys Tyr Gly Glu Gly Asn Trp Ser Lys Ile Leu Leu His
                20                  25                  30

Tyr Lys Phe Asn Asn Arg Thr Ser Val Met Leu Lys Asp Arg Trp Arg
            35                  40                  45

Thr Met Lys Lys Leu
            50
```

(2) INFORMATION FOR SEQ ID NO:16:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Val Lys Lys Ser Ser Trp Thr Glu Glu Glu Asp Arg Ile Ile Tyr Glu
1               5                   10                  15

Ala His Lys Arg Leu Gly Asn Arg Trp Ala Glu Ile Ala Lys Leu Leu
                20                  25                  30

Pro Gly Arg Thr Asp Asn Ser Ile Lys Asn His Trp Asn Ser Thr Met
            35                  40                  45

Arg Arg Lys
        50
```

(2) INFORMATION FOR SEQ ID NO:17:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Val Lys Lys Ser Cys Trp Thr Glu Glu Glu Asp Arg Ile Ile Cys Glu
1               5                   10                  15

Ala His Lys Val Leu Gly Asn Arg Trp Ala Glu Ile Ala Lys Met Leu
                20                  25                  30
```

```
        Pro  Gly  Arg  Thr  Asp  Asn  Ala  Val  Lys  Asn  His  Trp  Asn  Ser  Thr  Ile
                  35                       40                      45

Lys  Arg  Lys
                  50
```

( 2 ) INFORMATION FOR SEQ ID NO:18:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
        Val  Lys  Lys  Thr  Ser  Trp  Thr  Glu  Glu  Glu  Asp  Arg  Ile  Ile  Tyr  Gln
        1                 5                       10                      15

Ala  His  Lys  Arg  Leu  Gly  Asn  Arg  Trp  Ala  Glu  Ile  Ala  Lys  Leu  Leu
                       20                       25                      30

Pro  Gly  Arg  Thr  Asp  Asn  Ala  Ile  Lys  Asn  His  Trp  Asn  Ser  Thr  Met
                  35                       40                      45

Arg  Arg  Lys
                  50
```

( 2 ) INFORMATION FOR SEQ ID NO:19:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
        Ile  Lys  Lys  Thr  Ala  Trp  Thr  Glu  Lys  Glu  Asp  Glu  Ile  Ile  Tyr  Gln
        1                 5                       10                      15

Ala  His  Leu  Glu  Leu  Gly  Asn  Gln  Trp  Ala  Lys  Ile  Ala  Lys  Arg  Leu
                       20                       25                      30

Pro  Gly  Arg  Thr  Asp  Asn  Ala  Ile  Lys  Asn  His  Trp  Asn  Ser  Thr  Met
                  35                       40                      45

Arg  Arg  Lys
                  50
```

( 2 ) INFORMATION FOR SEQ ID NO:20:

( i ) SEQUENCE CHARACTERISTICS:
        ( A ) LENGTH: 148 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

```
GTACCCGGGG  ATCGTGACTC  TAGAGGGGCC  CTAACCCTAA  CCCTAACCCT  AACCCTAACC        60

CTAACCCTAA  CCCTAACCCT  AACCCTAACC  CTAACCCTAA  CCCTAACCCG  GGTCGAATTC       120

GATCTCTAGA  GTCGACCTGC  AGGCATGC                                             148
```

( 2 ) INFORMATION FOR SEQ ID NO:21:

( i ) SEQUENCE CHARACTERISTICS:

(A) LENGTH: 33 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:21:

GTCAAAAACT GACATATGTA TATCGTTCTC AAC    33

TELOMERE REPEAT BINDING FACTOR AND DIAGNOSTIC AND THERAPEUTIC USE THEREOF

GOVERNMENTAL SUPPORT

The research leading to the present invention was supported, in part, by a grant from the National Institutes of Health, No. GM49046. Accordingly, the United States Government may have certain rights in the present invention.

TECHNICAL FIELD OF THE INVENTION

The present invention relates generally to telomeric binding proteins, in particular to a telomeric repeat binding factor (TRF), to the nucleotide sequence encoding the TRF, and to diagnostic and therapeutic methods of use thereof. TRF has particular uses in the treatment of cancer and aging.

BACKGROUND OF THE INVENTION

Eucaryotic chromosomes end in specialized structures, called telomeres (Muller (1939) *The Collecting Net-Woods Hole* 13:181–195) that are thought to fulfill at least three functions. First, telomeres protect natural double-stranded DNA ends from degradation, fusion, and recombination with chromosome-internal DNA (McClintock (1941) *Genetics* 26:234–282). Second, cytogenetic observations indicate that telomeres are located at the nuclear periphery, suggesting a role for chromosome ends in the architecture of the nucleus (Agard et al (1983) *Nature* 302:676–681; Rabl (1885) *Morphol. J.* 10:214–330). Third, telomeres must provide a solution to the end-replication problem (Watson (1972) *Nature* 239:197–201): because all known polymerases require a primer and synthesize DNA from 5' to 3', the 3' ends of linear DNA pose a problem to the replication machinery.

The single common structural feature of most eucaryotic telomeres is the presence of a tandem array of G-rich repeats which, according to genetic studies in *Saccharomyces cerevisiae*, are necessary and sufficient for telomere function (Lundblad et al (1989) *Cell* 83:633–643; Szostak et al (1982) *Cell* 36:459–568). Although all telomeres of one genome are composed of the same repeats, the terminal sequences in different species vary. For instance, Oxytricha chromosomes terminate in TTTTGGGG repeats (Klobutcher et al (1981) *Proc. Natl. Acad. Sci. USA* 78:3015–3019), Tetrahymena utilizes an array of (TTGGGG)$_n$ (Blackburn et al (1978) *J. Mol. Biol.* 120:33–53), plant chromosomes carry the sequence (TTTAGGG)$_n$ (Richards et al (1988) *Cell* 53:127–136), and trypanosomes and mammals have TTAGGG repeats at their chromosome ends (Blackburn et al (1984) *Cell* 36:447–458; Brown (1986) *Nature* 338:774–776; Cross et al (1989) *Nature* 338:771–774; Moyzis et al (1988) *Proc. Natl. Acad. Sci. USA* 85:6622–6626; Van der Ploeg et al (1984) *Cell* 36:459–468). The organization of the telomeric repeats is such that the G-rich strand extends to the 3' end of the chromosome. At this position, telomerase, an RNA-dependent DNA polymerase, first demonstrated in *Tetrahymena thermophila* and other ciliates, can elongate telomeres, probably by using an internal RNA component as template for the addition of the appropriate G-rich sequence (Greider and Blackburn (1985) *Cell* 43:405–413). This activity is thought to complement the inability of polymerases to replicate chromosome ends, but other mechanisms of telomere maintenance may operate as well (Pluta et al (1989) *Nature* 337:429–433).

Proximal to the essential telomeric repeats, some chromosome ends harbor additional common elements called sub-telomeric repeats or telomere-associated sequences (Chart et al (1983) *Cell* 33:563–573; Corcoran et al (1988) *Cell* 53:807–813; de Lange et al (1983) *Nucl. Acids. Res.* 11:8149–8165; Van der Ploeg et al (1984); Dunn et al (1984) *Cell* 39:191–201). Unlike telomeric repeats, these sequences are not conserved and their function remains unclear (Murray et al (1986) *Mol. Cell. Biol.* 6:3166–3172).

Chromosome ends of unicellular organisms often show structural instability. Frequent rearrangements of subtelomeric sequences occur in trypanosomes (Borst (1986) *Annu. Rev. Biochem.* 55:701–732, de Lange et al (1983)), *S. cerevisiae* (Carlson et al (1983) *Mol. Cell. Biol.* 3:351–359; Horowitz et al (1984) *Mol. Cell. Biol.* 4:2509–2517), and plasmodia (Corcoran et al (1988)), and changes in the telomeric repeat region can be observed in protozoa (Bernards et al (1983) *Nature* 303:592–597; Pays (1983) *Nucl. Acids. Res.* 11:8137–8147; Van der Ploeg (1984)), ciliates (Larson et al (1987) *Cell* 50:477–483), and fungi (Carson et al (1985) *Cell* 42:249–257; Lundblad et al (1989); Lustig et al (1986) *Proc. Natl. Acad. Sci. USA* 83:1398–1402). As much as 3.5 kilobase pairs (kb) was seen to be added to telomeres of *Trypanosoma brucei* in a process that appears gradual and continuous, and was calculated to result from the addition of 6 to 10 base pairs (bp) per end per cell division (Bernards et al (1983); Pays et al (1983); Van der Ploeg (1984)). A similar gradual telomere elongation, compatible with the addition of telomeric repeats by telomerase, occurs in continuously growing *T. thermophila* (Larson (1987)) and a cell cycle mutant (cdc17) of *S. cerevisiae* (Carson et al (1985)). In wild-type *S. cerevisiae* (Shampay et al (1988) *Proc. Natl. Acad. Sci. USA* 85:534–538), however, and in *T. thermophila* grown in batch cultures (Larson et al (1998)), the tandem array of telomeric repeats is maintained at constant length. At least four genes (CDC17, EST1, TEL1, and TEL2 [Carson et al (1985); Lundblad et al (1989); Lustig et al (1986)] govern the length and stability of yeast telomeres; their mode of action is not understood.

Much less is known about the structure and behavior of chromosome ends of multicellular organisms. Mammalian telomeres have become amenable to molecular dissection with the demonstration that telomeric repeats of plants and *T. thermophila* species cross-hybridize to vertebrate chromosome ends (Allshire et al (1988) *Nature* 332:656–659; Richards et al (1988)). It has also been shown that human DNA contains tandem arrays of TTAGGG repeats, probably at the chromosome ends, providing further evidence for the evolutionary conservation of telomeres and a tool for the isolation of telomeric DNA (Moyzis et al (1988). Two strategies to obtain human chromosome ends have proven successful: an indirect isolation protocol that relies on human telomeres to be functional in *S. cerevisiae* (Brown et al (1989); Cross et al (1989)) and direct cloning in *E. coli*.

de Lange et al (*Mol. Cell. Biol.* 10:518–527, 1990) characterized the structure and variability of human autosomal chromosome ends. The chromosome ends they analyzed shared a sub-telomeric repeat of at least 4 kb that is not conserved in rodent genomes. These chromosome ends were characterized by a long stretch of DNA, of up to 14 kb, that lacks restriction enzyme cutting sites and may be entirely composed of TTAGGG repeats. From this region sequences are lost during development, leading to shortened, heterogeneously sized telomeres in somatic tissues, primary tumors, and most cell lines.

de Lange (*EMBO J.* 11:717–724, 1992) reported that human telomeres are tightly associated with the nuclear matrix. Telomeres were demonstrated to be anchored via their TTAGGG repeats. Moreover, TTAGGG repeats at internal sites within the chromosome do not behave as matrix-attached loci, suggesting that the telomeric position of the repeats is required for their interaction with the nuclear matrix. This evidence is consistent with the role of telomeres in a nucleoprotein complex.

TRF activity was first identified in 1992 by Zhong et al (*Mol. Cell. Biol.* 12:4834–4943) as a DNA-binding factor specific for TTAGGG repeat arrays. TRF was found to be present in nuclear extracts of human, mouse and monkey cells. The optimal site for TRF binding was found to contain at least six contiguous TTAGGG repeats. However, the protein isolated by Zhong et al was not sufficiently purified from other DNA-binding proteins such that its amino acid sequence could be determined.

Saltman et al (*Chromosoma* 102:121–128, 1993) characterized the molecular structure of telomeres of two human tumor cell lines with frequent end-to-end associations of metaphase chromosomes. Such end-to-end associations have been observed in a variety of human tumors, aging cells and several chromosome instability syndromes. The telomeres of such end-associated chromosomes were shown by Saltman et al to be severely reduced compared to other human cells with functional telomeres. However, other cell lines with severely shortened telomeres were not delectably compromised in their function. Thus, the investigators suggested that telomeric length was not the only determinant of the fusigenic behavior of human telomeres in tumor cells. A *Xenopus laevis* protein factor that specifically recognizes vertebrate telomeric repeats at DNA ends, termed Xenopus telomere end factor (XTEF) was identified by Cardenas et al in 1993 (*Genes and Devel.* 7:883–894). The DNA-binding properties of XTEF resembled the characteristics of a class of terminus-specific telomere proteins identified in hypotrichous ciliates.

There has been speculation on the role of an enzyme termed telomerase in human cancer, in particular in ovarian carcinoma (de Lange *Proc. Natl. Acad. Sci. USA* 91:2882–2885, 1994). Telomerases use the 3' end of DNA as a primer and employ an RNA template for the synthesis of G-rich telomeric repeats. Telomerase activation appears to be an obligatory step in the immortalization of human cells.

Hanish et al (*Proc. Natl. Acad. Sci. USA* 91:8861–8865) examined the requirements for the formation of human telomeres from TTAGGG seeds, and found that telomere formation was not correlated with the ability of human telomerase to elongate telomeric sequences in vitro, and did not appear to be a result of homologous recombination. Rather, the investigators reported that the sequence dependence of telomere formation matched the in vitro binding requirements for TRF.

Although the activity of TRF had been identified and isolated to some extent, the purification of TRF was fraught with difficulty, both in isolating the protein away from other DNA binding proteins, and in obtaining active protein from the isolate.

SUMMARY OF THE INVENTION

In view of the aforementioned deficiencies in prior art methods of isolating telomeric binding proteins, it is apparent that there exists a need for a method of purifying such proteins for the further molecular characterization thereof.

In accordance with the present invention, a nucleotide sequence encoding a human TRF is provided. The human TRF encoded by this nucleotide sequence has a high degree of homology to other vertebrate, i.e., mammalian TRFs, in particular murine TRF.

In a further embodiment, a method for purifying telomeric binding proteins is provided, which comprises the steps of:
a) isolating nuclei from tissue culture cells;
b) preparing nuclear extracts of the nuclei;
c) contacting the nuclear extracts with an affinity chromatography column comprising a bound DNA fragment, wherein the DNA fragment comprises TTAGGG repeat sequences; and
d) eluting telomeric binding proteins from the column.

In a particular embodiment, casein is added to the eluted telomeric binding proteins to obtain active DNA-binding proteins.

The present invention extends to TRFs having the following characteristics:
a) binding to telomere repeat sequences, in particular, TTAGGG repeats;
b) DNA binding activity in purified form in the presence of casein;
c) having a molecular weight of approximately 67 kD; and
d) exhibiting substantial sequence homology to Myb type DNA binding domains.

In a further aspect, the TRF may be used to alter telomere length, for example to increase telomere length during aging, and to decrease telomere length in the treatment of cancer. Accordingly, methods of providing TRF and its inhibitors or antagonists are contemplated.

In a specific example, the TRF nucleotide sequence is isolated from human or murine sources.

In a still further aspect, the present invention extends to antibodies and oligonucleotide probes to TRF, which may be used for both diagnostic and therapeutic approaches.

The present invention also relates to a recombinant DNA molecule or cloned gene, or a degenerate variant thereof, which encodes a TRF; preferably a nucleic acid molecule, in particular a recombinant DNA molecule or cloned gene, encoding the TRF has a nucleotide sequence or is complementary to a DNA sequence shown in FIG. 2A–2B (SEQ ID NO:11).

The human and murine DNA sequences of the TRF of the present invention or portions thereof, may be prepared as probes to screen for complementary sequences and genomic clones in the same or alternate species. The present invention extends to probes so prepared that may be provided for screening cDNA and genomic libraries for the TRF. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in FIG. 2 (SEQ ID NO:11). Correspondingly, the preparation of antisense RNA and ribozymes are included herein.

The present invention also includes TRF proteins having the activities noted herein, and that display the amino acid sequences set forth and described above in SEQ ID NO:12.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present TRF(s), and more particularly, the complete DNA sequence determined from the sequences set forth above and in SEQ ID NO:11.

According to other preferred features of certain preferred embodiments of the present invention, a recombinant expression system is provided to produce biologically active animal or human TRF.

The concept of the TRF contemplates that specific factors exist for binding to specific DNA sequences, such as the TTAGGG sequence and the like, as described earlier. Accordingly, the exact structure of each TRF will understandably vary so as to achieve this DNA binding and activity specificity. It is this specificity and the direct involvement of the TRF in the chain of events leading to telomere length regulation, that offers the promise of a broad spectrum of diagnostic and therapeutic utilities.

The present invention naturally contemplates several means for preparation of the TRF, including as illustrated herein known recombinant techniques, and the invention is accordingly intended to cover such synthetic preparations within its scope. The isolation of the cDNA amino acid sequences disclosed herein facilitates the reproduction of the TRF by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate TRF activity of target mammalian cells by interrupting or potentiating the activity of the TRF. In one instance, the test drug could be administered to a cellular sample containing the TRF along with telomeric sequences, to determine its effect upon the binding activity of the TRF to the DNA, or to the test drug, by comparison with a control.

The assay system could more importantly be adapted to identify drugs or other entities that are capable of binding to the TRF and/or other telomeric binding factors or proteins in the nucleus, thereby inhibiting or potentiating the activity of TRF. Such assay would be useful in the development of drugs that would be specific against particular cellular activity, or that would potentiate such activity, in time or in level of activity. For example, such drugs might be used to inhibit the proliferation of cells in cancerous states, or to treat cells which are aging, or to treat other pathologies associated with variations in telomere length.

In yet a further embodiment, the invention contemplates antagonists of the activity of a TRF, in particular, an agent or molecule that inhibits telomere function. In a specific embodiment, the antagonist can be a peptide having the sequence of a portion of a DNA binding domain of a TRF, such as that illustrated by SEQ ID NO:13.

The diagnostic utility of the present invention extends to the use of the present TRF in assays to screen for cancer and other inherited diseases associated with telomere length.

The present invention likewise extends to the development of antibodies against the TRF(s), including naturally raised and recombinantly prepared antibodies. For example, the antibodies could be used to screen expression libraries to obtain the gene or genes that encode the TRF(s). Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating telomere length.

Thus, the TRFs, their analogs and/or analogs, and any antagonists or antibodies that may be raised thereto, are capable of use in connection with various diagnostic techniques, including immunoassays, such as a radioimmunoassay, using for example, an antibody to the TRF that has been labeled by either radioactive addition, reduction with sodium borohydride, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the TRF, or to identify drugs or other agents that may mimic or block their activity. The system or test kit may comprise a labeled component prepared by one of the radioactive and/or enzymatic techniques discussed herein, coupling a label to the TRFs, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the TRF(s), its (or their) subunits, or active fragments thereof, or upon agents or other drugs determined to possess the same activity. A first therapeutic method is associated with the prevention of the manifestations of conditions causally related to or following from the binding activity of the TRF or its subunits, and comprises administering an agent capable of modulating the production and/or activity of the TRF or subunits thereof, either individually or in mixture with each other in an amount effective to prevent the development of those conditions in the host. For example, drugs or other binding partners to the TRF or proteins may be administered to inhibit or potentiate TRF activity, as in the potentiation of TRF activity in aging, or the inhibition or modulation of TRF activity in cancer therapy.

More specifically, the therapeutic method generally referred to herein could include the method for the treatment of various pathologies or other cellular dysfunctions and derangements by the administration of pharmaceutical compositions that may comprise effective inhibitors or enhancers of activation of the TRF or its subunits, or other equally effective drugs developed for instance by a drug screening assay prepared and used in accordance with a further aspect of the present invention. For example, drugs or other binding partners to the TRF or proteins, as represented by SEQ ID NO:12, may be administered to inhibit or potentiate telomere lengthening activity, as in the inhibition or modulation of TRF in cancer therapy.

In particular, the proteins of TRF whose sequences are presented in SEQ ID NO:12 herein, their antibodies, agonists, antagonists, or active fragments thereof, could be prepared in pharmaceutical formulations for administration in instances wherein anti-telomerase therapy is appropriate, such as to treat cancer.

Accordingly, it is a principal object of the present invention to provide a TRF and its subunits in purified form that exhibits certain characteristics and activities associated with telomere lengthening activity.

It is a further object of the present invention to provide antibodies to the TRF and its subunits, and methods for their preparation, including recombinant means.

It is a further object of the present invention to provide a method for detecting the presence of the TRF and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of the TRF and/or its subunits in mammals.

It is a still further object of the present invention to provide a method for the treatment of mammals to control the amount or activity of the TRF or subunits thereof, so as to alter the adverse consequences of such presence or activity, or where beneficial, to enhance such activity.

It is a still further object of the present invention to provide a method for the treatment of mammals to control the amount or activity of the TRF or its subunits, so as to treat or avert the adverse consequences of invasive, spontaneous or idiopathic pathological states.

It is a still further object of the present invention to provide pharmaceutical compositions for use in therapeutic methods which comprise or are based upon the TRF, its subunits, their binding partner(s), or upon agents or drugs that control the production, or that mimic or antagonize the activities of the TRF.

Other objects and advantages will become apparent to those skilled in the art from a review of the ensuing description which proceeds with reference to the following illustrative drawings.

BRIEF DESCRIPTION OF THE DRAWINGS

FIG. 1A–1B depicts peptide sequences derived from the purified TRF preparation (SEQ ID NOS:1–10).

FIG. 2A–2B depicts the nucleotide sequence of human TRF mRNA (SEQ ID NO:11). The Xho I site used for construction of expression constructs (in vitro and in vivo) is indicated. The sequence contains a Met ATG codon with the surrounding sequence AACATGG, which is as expected for an initiation codon. The encoded protein is 439 amino acids in length, with a predicted molecular weight of about 51 kD. The fact that this is somewhat smaller than the 67 kD protein observed on SDS-PAGE indicated that TRF may be modified or run anomalously on SDS-PAGE.

FIG. 3 depicts the deduced amino acid sequence of human TRF (SEQ ID NO:12). In italics is a region with a high percentage acidic residues ("acidic domain"), a hallmark of transcription factors. Underlined are the regions determined by peptide sequencing. Bolded is the region of homology to Myb type DNA binding repeats.

FIG. 4 depicts the alignment of human TRF sequence to Myb type DNA binding domains (SEQ ID NOS:13–19). Hu=human, Mu=mouse and Dro=Drosophila.

FIG. 7A–7B depicts various staining patterns on HeLa cells. FIG. 7A shows a FLAG epitope tagged mouse TRF expressed in human HeLa cells. Shown is two interphase nuclei in which the anti-FLAG antibodies detect a speckled TRF pattern (green) against the background of DAPI stained DNA (blue). FIG. 7B shows in situ hybridization of telomeric TTAGGG DNA (red) in the nuclei shown in A. FIG. 7C shows superimposed images from FIGS. 7A and 7B, demonstrating that all signals co-localize. FIG. 7D shows HA epitope tagged mouse TRF expressed in human HeLa cells. Shown is a metaphase spread in which the anti-HA antibody detects TRF at each chromosome end (green). The DNA is stained with DAPI (blue).

DETAILED DESCRIPTION

Figure 5:
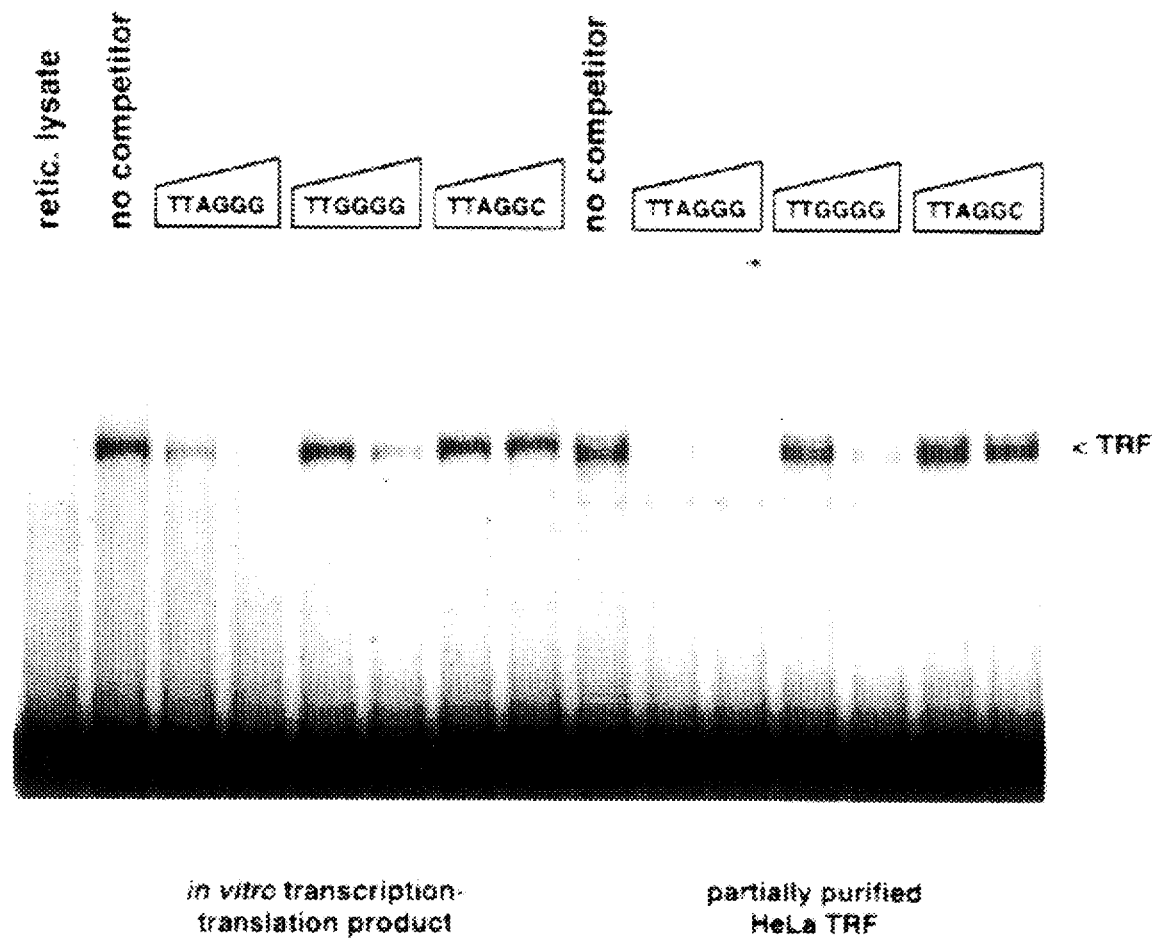
FIG. 5 depicts a gel-shift experiment showing telomeric repeat binding activity of protein encoded by the human HTRF4.1 cDNA. The human cDNA was fused onto a His6 tag and a initiator codon and expressed by in vitro transcription (T7 RNA polymerase) and translation in a rabbit reticulocyte lysate. No gel shift complex is formed in the absence of human TRF cDNA. The probe is a $(TTAGGG)_{12}$ containing restriction fragment. Competitions were done with plasmids containing long arrays of telomeric DNAs with the indicated sequence. Gel-shift methods are as described by (Zhong et al (1992) *Mol. Cell Biol.* 13:4834–4843). The data indicate that the human TRF binds TTAGGG repeats with the same sequence specificity as HeLa TRF activity.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "telomere repeat binding factor," "telomeric binding factor," "TRF," and any variants not specifically listed, may be used herein interchangeably, and as used throughout the present application and claims refer to proteinaceous material including single or multiple proteins, and extends to those proteins having the amino acid sequence data described herein and presented in FIG. 3 (SEQ ID NO:12), and the profile of activities set forth herein and in the claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "telomere repeat binding factor," and "TRF" are intended to include within their scope proteins specifically recited herein as well as all substantially homologous analogs and allelic variations.

The amino acid residues described herein are preferred to be in the "L" isomeric form. However, residues in the "D"

isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

It should be appreciated that also within the scope of the present invention are DNA sequences encoding TRF which code for a TRF having the same amino acid sequence as SEQ ID NO:12, but which are degenerate to SEQ ID NO:12. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Termination codon | UAA (ochre) or UAG (amber) or UGA (opal) |

It should be understood that the codons specified above are for RNA sequences. The corresponding codons for DNA have a T substituted for U.

Mutations can be made in SEQ ID NO:11 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino acids with nonpolar R groups

Alanine

Valine

Leucine

Isoleucine

Proline

Phenylalanine

Tryptophan

Methionine

Amino acids with uncharged polar R groups

Glycine

Serine

Threonine

Cysteine

Tyrosine

Asparagine

Glutamine

Amino acids with charged polar R groups (negatively charged at Ph 6.0)

Aspartic acid

Glutamic acid

Basic amino acids (positively charged at pH 6.0)

Lysine

Arginine

Histidine (at pH 6.0)

Another grouping may be those amino acids with phenyl groups:

Phenylalanine

Tryptophan

Tyrosine

Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and Gln for Asn such that a free $NH_2$ Call be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. Likewise, two polypeptide sequences are "substantially homologous" when at least about 75% (preferably at least about 80%, and most preferably at least about 90 or 95%) of the amino acids are either identical or contain conservative changes, as defined above, over the defined length of the polypeptide sequences.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash.

The term "approximately" means that the value may vary by 10%, preferably no more than 5%, and most preferably no more than 2%.

In its primary aspect, the present invention concerns the identification of a TRF.

As stated above, the present invention also relates to a recombinant DNA molecule or cloned gene, or a degenerate variant thereof, which encodes a TRF, or a fragment thereof, that possesses a molecular weight of about approximately 67 kD and an amino acid sequence set forth in FIG. 3 (SEQ ID NO:12); preferably a nucleic acid molecule, in particular a recombinant DNA molecule or cloned gene, encoding the 67 kD TRF has a nucleotide sequence or is complementary to a DNA sequence shown in FIG. 2A–2B (SEQ ID NO:11).

The possibilities both diagnostic and therapeutic that are raised by the existence of the TRF, derive from the fact that the factors appear to participate in direct and causal protein-DNA interaction between the repeat sequences that are bound by their binding factors, and those factors that thereafter directly interface with the DNA repeat sequence and effect telomere length and accordingly the health and/or proliferative capacity of the cell. As suggested earlier and elaborated further on herein, the present invention contemplates pharmaceutical intervention in the cascade of reactions in which the TRF is implicated, to modulate the activity initiated by the binding factor bound to the repeat sequence.

Thus, in instances where it is desired to reduce or inhibit the length or function of a telomere resulting from a particular stimulus or factor, an appropriate inhibitor of the TRF could be introduced to block the interaction of the TRF with those repeat sequences causally connected with telomere lengthening or function. Correspondingly, instances where insufficient telomere length is present could be remedied by the introduction of additional quantities of the TRF or its chemical or pharmaceutical cognates, analogs, fragments and the like to restore telomere function.

As discussed earlier, the TRF or their binding partners or other ligands or agents exhibiting either mimicry or antagonism to the TRF or control over their production, may be prepared in pharmaceutical compositions, with a suitable carrier and at a strength effective for administration by various means to a patient experiencing an adverse medical condition associated with abnormal telomere length, stimulation for the treatment thereof. A variety of administrative techniques may be utilized, among them parenteral techniques such as subcutaneous, intravenous and intraperitoneal injections, catheterizations and the like. Average quantities of the TRFs or their subunits may vary and in particular should be based upon the recommendations and prescription of a qualified physician or veterinarian.

Also, antibodies including both polyclonal and monoclonal antibodies, and drugs that modulate the production or activity of the TRF and/or their subunits may possess certain diagnostic applications and may for example, be utilized for the purpose of detecting and/or measuring conditions such as viral refection or the like. For example, the TRF or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the TRF of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against TRF peptides can be screened for various properties; i.e., isotype, epitope, affinity, etc. Of particular interest are monoclonal antibodies that neutralize the binding activity of the TRF or its subunits. Such monoclonals can be readily identified in, for example, gel-shift assays. High affinity antibodies are also useful when immunoaffinity purification of native or recombinant TRF is possible.

Preferably, the anti-TRF antibody used in the diagnostic methods of this invention is an affinity purified polyclonal antibody. More preferably, the antibody is a monoclonal antibody (mAb). In addition, it is preferable for the anti-TRF antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to a TRF protein, such as an anti-TRF antibody, preferably an affinity-purified polyclonal antibody, and more preferably a mAb. In addition, it is preferable for the anti-TRF antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, a viral infection or other like pathological derangement. Methods for isolating and inducing anti-TRF antibodies and for determining and optimizing the ability of anti-TRF antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in Antibodies—A Laboratory Manual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a TRF-binding portion thereof, or TRF, or a DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present TRF and their ability to inhibit specified activity at telomeres in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

Methods for producing monoclonal anti-TRF antibodies are also well-known in the art. See Niman et al., Proc. Natl. Acad. Sci. USA, 80:4949–4953 (1983). Typically, the present TRF or a peptide analog is used either alone or conjugated to an immunogenic carrier, as the immunogen in the before-described procedure for producing anti-TRF monoclonal antibodies. The hybridomas are screened for the ability to produce an antibody that immunoreacts with the TRF peptide analog and the present TRF.

The present invention further contemplates therapeutic compositions useful in practicing the therapeutic methods of this invention. A subject therapeutic composition includes, in admixture, a pharmaceutically acceptable excipient (carrier) and one or more of a TRF, polypeptide analog thereof or fragment thereof, as described herein as an active ingredient. In a preferred embodiment, the composition comprises an antigen capable of modulating the specific binding of the present TRF within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the tree carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of TRF binding capacity desired.

Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the TRF antagonist or analog thereof, and one or more of the following active ingredients: an antibiotic, asteroid. Exemplary formulations are given below:

| Ingredient | mg/ml |
|---|---|
| Formulations | |
| Intravenous Formulation I | |
| cefotaxime | 250.0 |
| TRF | 10.0 |
| dextrose USP | 45.0 |
| sodium bisulfite USP | 3.2 |
| edetate disodium USP | 0.1 |
| water for injection q.s. a.d. | 1.0 ml |
| Intravenous Formulation II | |
| ampicillin | 250.0 |
| TRF | 10.0 |
| sodium bisulfite USP | 3.2 |
| disodium edetate USP | 0.1 |
| water for injection q.s. a.d. | 1.0 ml |
| Intravenous Formulation III | |
| gentamicin (charged as sulfate) | 40.0 |
| TRF | 10.0 |
| sodium bisulfite USP | 3.2 |
| disodium edetate USP | 0.1 |
| water for injection q.s. a.d. | 1.0 ml |
| Intravenous Formulation IV | |
| TRF | 10.0 |
| dextrose USP | 45.0 |
| sodium bisulfite USP | 3.2 |
| edetate disodium USP | 0.1 |
| water for injection q.s. a.d. | 1.0 ml |
| Intravenous Formulation V | |
| TRF antagonist | 5.0 |
| sodium bisulfite USP | 3.2 |
| disodium edetate USP | 0.1 |
| water for injection q.s. a.d. | 1.0 ml |

As used herein, "pg" means picogram, "ng" means nanogram, "ug" or "μg" mean microgram, "mg" means milligram, "ul" or "μl" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAS, e.g., the numerous derivatives of phage λ, e.g., NM989, and other phage DNA, e.g., M13 and Filamentous single stranded phage DNA; yeast plasmids such as the 2μIt plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences— sequence that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, RI.I, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that TRF analogs may be prepared from nucleotide sequences of the protein complex/subunit derived within the scope of the present invention. Analogs, such as fragments, may be produced, for example, by pepsin digestion of TRF material. Other analogs, such as muteins, can be produced by standard site-directed mutagenesis of TRF coding sequences. Analogs exhibiting "TRF activity" such as small molecules, whether functioning as promoters or inhibitors, may be identified by known in vivo and/or in vitro assays.

As mentioned above, a DNA sequence encoding a TRF can be prepared synthetically rather than cloned. The DNA sequence can be designed with the appropriate codons for the TRF amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express TRF analogs or "muteins". Alternatively, DNA encoding muteins can be made by site-directed mutagenesis of native TRF genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244:182–188 (April 1989). This method may be used to create analogs with unnatural amino acids.

The present invention extends to the preparation of antisense nucleotides and ribozymes that may be used to interfere with the expression of the TRF at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988). In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into TRF-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for TRF and their ligands.

The present invention also relates to a variety of diagnostic applications, including methods for detecting the presence of stimuli such as the earlier referenced polypeptide ligands, by reference to their ability to elicit the activities which are mediated by the present TRF. As mentioned earlier, the TRFs can be used to produce antibodies to itself by a variety of known techniques, and such antibodies could then be isolated and utilized as in tests for the presence of particular activity of TRF at telomeres in suspect target cells.

As described in detail above, antibody(ies) to the TRF can be produced and isolated by standard methods including the well known hybridoma techniques. For convenience, the antibody(ies) to the TRF will be referred to herein as $Ab_1$ and antibody(ies) raised in another species as $Ab_2$.

The presence of TRF in cells can be ascertained by the usual immunological procedures applicable to such determinations. A number of useful procedures are known. Three such procedures which are especially useful utilize either the TRF labeled with a detectable label, antibody $Ab_1$ labeled with a detectable label, or antibody $Ab_2$ labeled with a detectable label. The procedures may be summarized by the following equations wherein the asterisk indicates that the particle is labeled, and "T" stands for the TRF:

A. $T^* + Ab_1 = T^*Ab_1$
B. $T + Ab^* = TAb_1$
C. $T + Ab_1 + Ab_2^* = TAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the TRF forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-TRF antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The TRF or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the TRF may be radiolabeled and combined, for example, with antibodies or other inhibitors thereto, after which binding studies would be carried out. Solutions would then be prepared that contain various quantities of labeled and unlabeled uncombined TRF, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

In a further embodiment of this invention, commercial test kits suitable for use by a medical specialist may be prepared to determine the presence or absence of predetermined telomere-binding activity or predetermined telomere lengthening activity capability in suspected target cells. In accordance with the testing techniques discussed above, one class of such kits will contain at least the labeled TRF or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for binding activity to telomeres, comprising:

(a) a predetermined amount of at least one labeled immunochemically reactive component obtained by the direct or indirect attachment of the present TRF or a specific binding partner thereto, to a detectable label;

(b) other reagents; and (c) directions for use of said kit.

More specifically, the diagnostic test kit may comprise:

(a) a known amount of the TRF as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the TRF to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the TRF and a specific binding partner thereto.

In accordance with the above, an assay system for screening potential drugs effective to modulate the activity of the TRF may be prepared. The TRF may be introduced into a test system, and the prospective drug may also be introduced into the resulting cell culture, and the culture thereafter examined to observe any changes in the telomere lengths of chromosomes in the cells, due either to the addition of the prospective drug alone, or due to the effect of added quantities of the known TRF.

PRELIMINARY CONSIDERATIONS

Vertebrate telomeres contain 2-100 kb of tandem GGTTAG repeats. This telomeric nucleotide sequence is specified by the 5' CUAACC 3' template within the RNA component of vertebrate telomerases. Telomerase-mediated addition of GGTTAG repeats to the 3' chromosome ends can balance the loss of terminal sequences that occurs during replication of linear DNAs. The telomeric repeat array is essential for the stability of mammalian chromosomes. Without this protective cap, chromosome termini might activate DNA damage checkpoints, or be attacked by DNA repair functions leading to chromosome end fusion and degradation. This protective function of vertebrate telomeres is thought to result from the interaction of the telomeric GGTTAG repeats with telomere specific proteins. In support of this notion, telomeres in yeast and hypotrichous ciliates are known to contain protein components, telomeres have a unique chromatin structure (Tommerup et al (1994) Mol. Cell Biol. 14:5777-5785), and the sequence requirements for formation of new telomeres in human cells are highly specific (Hanish et al (1994) Proc. Natl. Acad. Sci. USA 91:8861-8865), as would be expected if the GGTTAG repeats interact with a sequence specific DNA binding protein (de Lange (1995) Seminars in Cell Biology 7, in press).

A search for telomeric proteins in vertebrate cells was therefore initiated. Since homologs of the telomeric proteins from unicellular organisms have not been found in vertebrates, biochemical approaches were taken to identify GGTTAG sequence specific DNA binding proteins. Several groups identified abundant proteins that interact with single-stranded GGTTAG repeats but these factors turned out to be hnRNP components that probably have a function in RNA metabolism rather than at telomeres (Ishikawa et al (1993) Mol. Cell Biol. 13:4301-4310; McKay et al (1992) Nucl. Acids Res. 20:1387-1391; McKay et al (1992) Nucl. Acids Res. 20:6461-6464).

The present invention uses double-stranded telomeric sequences to probe HeLa nuclear extracts for the presence of sequence-specific DNA binding proteins and has identified one candidate activity, called here Telomeric Repeat Binding Factor or TRF (Zhong et al (1992) Mol. Cell Biol. 13:4834-4843, incorporated herein by reference in its entirety). TRF was identified as a gel-shift activity that forms a specific complex with probes containing 3 or more tandem TTAGGG repeats. The sequence specificity of TRF is apparent from competition experiments in which the TRF gel-shift complex is easily competed out with TTAGGG repeat DNA but not with closely related telomeric sequences from other organisms, such as TTGGGG, and TTAGGC repeats. A TRF-like activity was found in all mammalian nuclear extracts that were examined, including extracts from a variety of human cell lines, human peripheral blood leukocytes, and extracts from monkey, mouse, hamster, and chicken cells (Zhong et al. 1992; unpublished observations by Chong and de Lange). The sequence specificity of TRF and its ubiquitous expression were as expected for a vertebrate telomeric protein.

A series of molecular genetic experiments also suggested that TRF interacts with telomeric DNA in human cells (Hanish et al (1994) Proc. Natl. Acad. Sci. USA 91:8861-8865). In these experiments de novo formation of human telomeres was induced by transfection of telomeric repeat sequences into human cells. Upon transfection of 0.8 kb or more of TTAGGG repeat DNA into human HeLa cells, approximately 70% of the transfected cell lines will carry a new telomere. However, when stretches of TTGGGG repeats, TTAGGC repeats or other closely related sequences are transfected, telomere formation is not observed in any of the cell lines examined. These stringent sequence requirements for telomere formation in human cells closely follow the sequence preference of TRF (Hanish et al, 1994). No other factor that is currently known can explain this dependence on precise TTAGGG repeat in the process of de novo telomere formation. Therefore, it seems likely that the incoming TTAGGG repeats require the interaction with TRF to form a new telomere. This is as expected if TRF is an integral component of mammalian telomeres.

TRF is the first telomeric protein isolated from human, any other vertebrate cell, or any other multicellular organism. Uses for the TRF include those related to the involvement of telomeres in human cancer and aging. Human telomeres shorten during normal cell divisions and telomere shortening may eventually limit cell proliferation and lead to aging. In cancer cells, telomere shortening may lead to genome instability. Many human cancer cells contain the enzyme telomerase that can restore telomere length.

Inhibition of TRF in human tumors is expected to lead to loss of telomere function. This loss of telomere function could limit the growth of tumor cells. Inhibition of TRF could be achieved by anti-sense approaches. In addition, TRF inhibition could be used in combination with anti-telomerase therapy. Anti-telomerase drugs are presently being developed. However, such drugs may not have an acute cytotoxic phenotype because it takes some time to lose enough telomeric DNA after inhibition of telomerase. Dual inhibition of both TRF and telomerase may synergize the effects of either drug.

The presence of TRF on telomeres may be a good indicator of the function of human telomeres. Since telomeres change in length during tumorigenesis, TRF staining of chromosome ends in human tumors may be able to reveal aspects of the stage of the tumor. Moreover, loss of TRF function or changes in TRF function are predicted to destabilize the genome and may contribute to tumorigenic transformation. TRF may therefore be an oncogene. As such, TRF has diagnostic and therapeutic uses in cancer diagnosis and treatment. By analogy to the function of the telomeric protein RAP1 in yeast, TRF is expected to control telomere length. Therefore, TRF could be a target for therapies that aim to change telomere length. In addition, it is possible that mutations in TRF would be responsible for certain genome instability syndromes. In the cases of families with mutations in TRF, TRF could be useful for diagnostic purposes and also for gene therapy.

Since telomerase and TRF are both involved in telomere function, it is possible that these proteins interact directly. TRF may therefore be used to isolate telomerase proteins. Moreover, the telomeric complex is likely to contain a number of protein components, and TRF is likely to interact with some of these. Therefore, TRF can be used to isolate other telomeric proteins that may have the same sort of commercial uses as TRF itself.

EXAMPLE 1

Purification of TRF protein. TRF was isolated from nuclear extract from HeLa cells (see Zhong et al, 1992, for preparation of nuclear extract). The following general strategy was used:

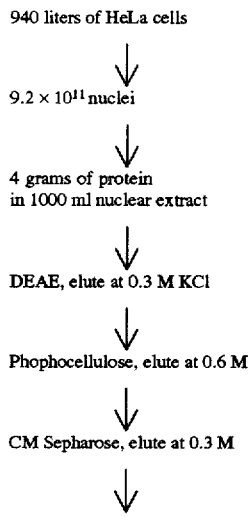

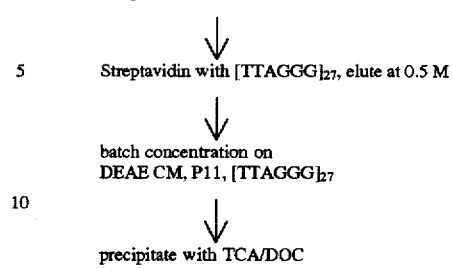

The use of a $[TTAGGG]_{27}$ repeat column greatly facilitated the purification of TRF. The column contains restriction fragments derived from a plasmid that was constructed by the present inventors, $p[TTAGGG]_{27\times 6}$. This plasmid contains an tandem array of six restriction fragments that are identical and each carry 27 TTAGGG repeats. The plasmid is digested with Asp 718 restriction enzyme and the ends of the fragments are labelled with Bio-dUTP and coupled onto Sepharose-Streptavidin. This is the only column material which allowed the separation of TRF from other DNA binding proteins.

A significant finding was that TRF does not bind DNA when it is highly purified. Thus, during isolation of the protein all DNA binding activity disappears. It was discovered that the DNA binding activity could be rescued by adding back bovine b-casein and a select set of other proteins. The addition of casein to TRF preparations during the purification thus appeared to be a necessary element of the isolation.

DETAILED DESCRIPTION OF THE PURIFICATION

TRF was isolated from a total of $9.2\times 10^{11}$ HeLa Cells, equivalent to 940 liters of culture (in Joklik's Media, supplemented with bovine calf serum, 2 mM L-glutamine, 0.1 mM non-essential amino acids, and penicillin/streptomycin). A nuclear extract containing 4 grams of protein and about 650 pmol of TRF (1 pmol TRF is defined as the amount of protein required to complex 1 pmol of labelled probe), as determined by quantitation using a PhosphoImager, was obtained from the cells and the soluble fraction was then purified over a series of ion exchange and affinity columns, as noted above. For each column, the sample was loaded in buffer containing 100 mM KCl and the flow-through was reloaded. The columns were developed in buffer with increasing potassium chloride salt concentration, with a final stripping of the column with 1M salt. All fractions were dialyzed to 100 mM KCl, 20 mM HEPES, 3 mM $MgCl_2$, 20% glycerol, and 0.1% NP-40 (nonidet-P40). Activity was determined by gel shift assay using a probe of 145 bp fragment containing $(TTAGGG)_2$ having the following sequence (SEQ D NO:21):

```
5'-GTA CCC GGG GAT CGT GAC TCT AGA GGG GCC CTA ACC CTA
ACC CTA ACC CTA ACC CTA ACC CTA ACC CTA ACC CTA ACC CTA
ACC CTA ACC CTA ACC CTA ACC CTA ACC CGG GTC GAA TTC GAT
CTC TAG AGT CGA CCT GCA GGC ATG C-3'
```

The nuclear extract was divided in half and the first 4 columns were run in duplicate. A 530 ml sample was applied onto a 200 ml DEAE column (diethenyl benzene, anion exchanger with 0.45–0.90 μm particle size, EM Separations) and TRF eluted at 0.2–0.3M KCl. Fractions were collected in 100 ml aliquots. The active fractions were pooled (226 ml, 201 mg protein, 131 pmol TRF) and applied onto a 200 ml P11, phosphocellulose column (cation exchanger with fiber length 50–250 µm, Whatman). To activate the column the P11 resin was incubated in NaOH for 1 minute, HCl for 1 minute, then neutralized in HEPES, pH 7.9. TRF activity was found in 0.6M fractions. These fractions were then combined (125 ml, 14 mg protein) and then run over a 4 ml CM Sepharose column (cross-linked agarose, 6%, cation exchanger, 45–165 µm). TRF eluted at 0.4–0.5M KCl. The 4.5 ml of active fractions collected were run on a 4.5 ml non-specific DNA column. This column is composed of Biotin-labelled, Hinf I digested E. coli chromosomal DNA bound to streptavidin beads. TRF activity eluted at 0.2–0.3 mM KCl. At this point, the active tractions were combined from the duplicate purification schemes run in parallel and the rest of the purification was completed using 1 of each subsequent column. The affinity column is a biotin-labelled, Asp 718 digested DNA bound to streptavidin beads, with (TTAGGG)$_{27}$ plasmid DNA.

A 4.5 ml sample was loaded onto a 0.5 ml affinity column and the activity eluted into 0.5M KCl fractions. This fraction was supplied with casein (50 µg) and batch-wise bound to DEAE, CM, and P11 columns. The final fraction was bound to 100 µl of (TTAGGG)$_{27}$ column material and eluted at 0.5M KCl. This active sample was precipitated with 20% trichloroacetic acid and 0.015% deoxycholate and then run on an SDS-PAGE gel and transferred to nitrocellulose. The 67 kD band was cut out, trypsinized, and sequenced.

EXAMPLE 2

Peptide sequence analysis and isolation of TRF cDNAs. Approximately 3 micrograms TRF protein of a MW of 67 kD was isolated. The partial amino acid sequences of a number of TRF peptides was determined (FIG. 1A–1B). One of these sequences (T29) was used for a search of the databases and identified two anonymous human cDNA fragments present in the databases at that time. The Genbank accession number of these sequence are: Z19923 and Z45971.

Based on the nucleotide sequence of the anonymous cDNA fragment Z19923, a 33 nucleotide synthetic DNA probe was synthesized that overlaps the T29 peptide sequence. This probe was end-labelled and used to screen a commercial HeLa cDNA library (from Stratagene). The sequence of this probe is:

5' GTCAAAAACTGACATATGTATATCGTTCTCAAC 3' (SEQ ID NO:21)

From the screen of the HeLa cDNA library a candidate TRF cDNA was isolated (clone 11.2). The insert in this clone was subsequently used to rescreen the HeLa cDNA library. Sequence analysis of the longest human cDNAs resulted in the identification of an open reading frame that contained all peptide sequences previously identified.

The human TRF cDNA 4.1 was used to screen a Stratagene mouse cDNA library. One of the resulting clones, #12, was partially sequenced and showed a high degree of sequence similarity to the human cDNA. The MTRF12 cDNA contains an open reading frame that begins with an initiator codon that conforms the Kozak rules, indicating that this is the N-terminus of the mouse TRF reading frame. That this clone indeed encodes full length mouse TRF proteins is further substantiated by the fact that TRF gel-shift complex encoded by this cDNA co-migrates with genuine mouse TRF from cultured J558 cells (see below).

The mouse and human sequences are very similar, allowing alignment of the two reading frames. The cDNA sequence of the human cDNA sequence and deduced open reading frame are given in FIGS. 2A–2B and 3, respectively.

EXAMPLE 3

TRF contains a Myb type DNA binding domain. The TRF sequence was used to execute database searches and a similarity to Myb type DNA binding domains was noted (FIG. 4).

EXAMPLE 4

Proof that the cDNAs encode TRF activity. One of the human cDNAs (HTRF4.1) was used to construct a fusion protein in which part of the TRF open reading frame from the N-terminal Xho I site to the natural termination codon at the Hind III site was inserted into the pET28b His6Tag expression vector from Novagen (Madison, Wis.). This new, chimeric open reading frame contained an initiator ATG codon with "Kozak rules" environment at its 5' end as well as an T7 RNA polymerase promoter sequence upstream. This construct was used for in vitro coupled transcription/translation (using a kit from Promega) resulting in synthetic protein (labelled with $^3$S methionine) with an apparent molecular weight (MW) of 60 kD. The in vitro synthesized protein was used in a gel-shift assay with a double stranded (TTAGGG)$_2$ repeat probe and shown to form a complex that migrates close to the HeLa TRF gel-shift complex. The in vitro synthesized protein was shown to have the same sequence specificity as TRF; i.e., it bound to TTAGGG repeats but not to TTGGGG or TTAGGC repeats (FIG. 5).

Figure 6:
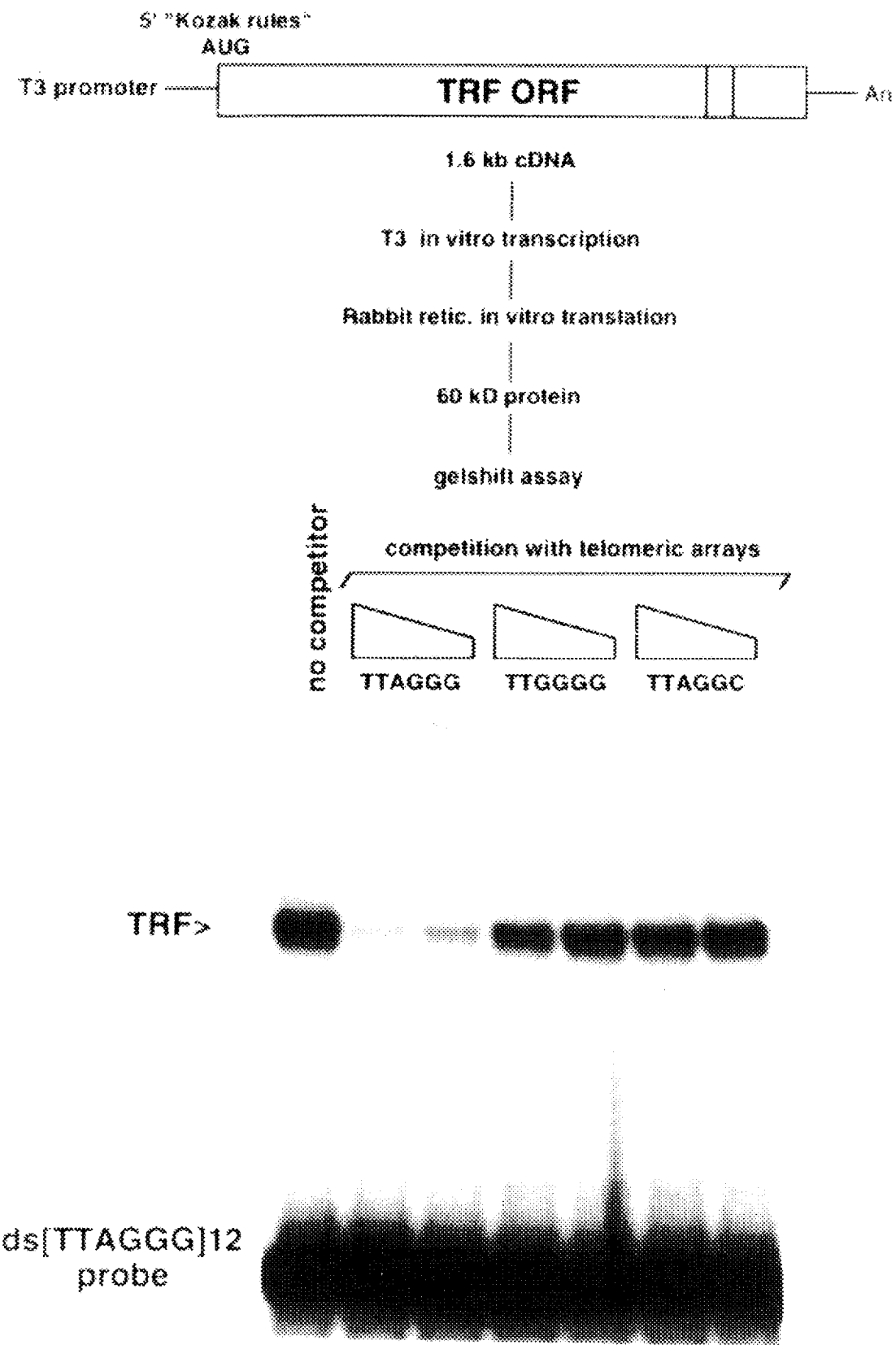
FIG. 6 depicts a gel-shift experiment showing telomeric repeat binding activity of protein encoded by the mouse MTRF12 cDNA. The cDNA was transcribed using T3 RNA polymerase and translated in a rabbit reticulocyte lysate. The probe is a $(TTAGGG)_{12}$-containing restriction fragment. Competitions were done with plasmids containing long arrays of telomeric DNAs with the indicated sequence. Gel-shift methods are as described by (Zhong et al. 1992).

The mouse cDNA (MTRF12) contained its own initiator codon and was transcribed and translated without further modification using the T3 promoter in its pBluescript vector. Similar to the human cDNA, a ~60 kD protein was synthesized that bound TTAGGG repeats but not TYGGGG or TTAGGC repeats (FIG. 6). The gel-shift complex obtained with MTRF-12 encoded protein co-migrates with the gel-shift complex formed with J558 mouse TRF, indicating that MTRF12 encodes full length TRF protein.

EXAMPLE 5

Proof that TRF is a telomeric protein
Staining of metaphase chromosome ends
Using the mouse TRF cDNA (MTRF12), a gene was constructed encoding the TRF protein tagged at the N-terminus with the HA antibody tag. This gene was endowed with the cytomegalovirus promoter and a Bovine Growth Hormone poly A addition site and transfected into a HeLa cell line which had previously been shown to have long telomeres (de Lange (1992) EMBO J. 11:717–724; de Lange et al (1990) Mol. Cell Biol. 10:518–527). The construct also contained a neomycin marker gene, allowing selection of stably transfected HeLa cells in the presence of 300 µg/ml G418. Clonal cell lines that expressed the HA-tagged TRF were isolated and used to make metaphase chromosome spreads (using colcemid block and cytospin technique for spreading). Staining for the HA-tagged TRF was achieved using a monoclonal anti-HA antibody and a FITC labelled secondary goat anti-mouse antibody. Signals are noted at the ends of all metaphase chromosomes (FIG. 7). No other signals are seen. Control experiments with HeLa cells without the HA-TRF construct do not show telomeric staining.

EXAMPLE 6

Co-localization of TRF and telomeric DNA in interphase nuclei. In a second line of evidence that TRF is exclusively located at telomeres it was shown that TTAGGG repeat DNA and epitope TRF co-localize in interphase cells. For these experiments MTRF12 was used to construct a FLAG tagged derivative fusion protein expressed from the CMV promoter.

This construct was transiently transfected (by electroporation) into HeLa cells with long telomeres (see preceding paragraph) and the cells were fixed 24 hours post-transfection with 2% formaldehyde. The telomeric DNA in these nuclei was detected through the annealing of a 150 nucleotide RNA containing CCCUAA repeats (the template is one of the TTAGGG repeat clones described in de Lange et al. 1990) that was synthesized in vitro in the presence of digoxygenin labelled rUTP and detected with sheep anti-digoxygenin primary antibody and a TRITC labelled donkey anti-sheep secondary antibody. The FLAG-tagged TRF was detected with a monoclonal mouse anti-FLAG antibody followed by a FITC labelled goat anti-mouse antibody. Both signals (TRITC and FITC) showed a speckled fully overlapping pattern, indicating complete co-localization of TRF with telomeric DNA (FIG. 7).

The following is a list of documents related to the above disclosure and particularly to the experimental procedures and discussions.

1. Tommerup, H., Dousmanis, A & de Lange, T. (1994) *Mol. Cell Biol.* 14:5777–5785.
2. Hanish, J. P., Yanowitz, J. & de Lange, T (1994) *Proc. Natl. Acad. Sci. USA* 91:8861–8865.
3. de Lange, T. (1996) *Seminars in Cell Biology* 7, in press.
4. Ishikawa, F., Matunis, M. J., Dreyfuss, G. & Cech, T. R. (1993) *Mol. Cell Biol.* 13:4301–4310.
5. McKay, S. J. & Cooke, H. (1992) *Nucl. Acids Res.* 20:1387–1391.
6. Mckay, S. J. & Cooke, H. (1992) *Nucl. Acids Res.* 20:6461–6464.
7. Zhong, Z., Shiue, L., Kaplan, S. & de Lange, T. (1992) *Mol. Cell Biol.* 13:4834–4843.
8. de Lange, T (1992) *EMBO J.* 11:717–724.
9. de Lange, T., Shiue, L., Myers, R. M., Cox, D. R., Naylor, S. L., Killery, A. M. & Varmus, H. E. (1990) *Mol. Cell Biol.* 10:518–527.
10. de Lange, T. (1995) "Telomere Dynamics and Genome Instability in Human Cancer," in *Telomeres*, Cold Spring Harbor Monograph, E. H. Blackburn and C. W. Greider, Eds.
11. Broccoli, D., Young, J. W., de Lange, T. (1995) "Telomerase activity in normal and malignant hematopoietic cells," *Proc. Natl. Acad. Sci. USA*, in press.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A vertebrate telomere repeat binding factor TRF in survived form having an amino acid sequence substantially homologous to that of SEQ ID NO:12 and having the following characteristics:
   a) it binds to telomere repeat sequence when it is highly purified form;
   b) it does not bind DNA when it is highly purified, but its DNA binding activity can be rescued in the presence of casein; and
   c) it is a member of the Myb family of DNA binding proteins.

2. The vertebrate TRF of claim 1, which is derived from mammalian cells.

3. The vertebrate TRF of claim 1 labeled with a detectable label.

4. The vertebrate TRF of claim 3 wherein the label is selected from the group consisting of an enzyme, a chemical which fluoresces, and a radioactive element.

5. A method of purifying a TRF from mammalian cells comprising:
   a) isolating nuclei from mammalian tissue culture cells;
   b) preparing nuclear extracts of the nuclei;
   c) contacting the nuclear extracts with an affinity chromatography column comprising a bound DNA restriction fragment, wherein the bound DNA restriction fragment comprises TTAGGG repeat sequences and the TRF binds to the bound DNA restriction fragment; and
   d) eluting the TRF from the bound DNA restriction fragment of the column.

6. The method of claim 5, wherein the TTAGGG repeat sequence are $(TTAGGG)_{27}$.

7. The method of claim 5, further comprising addition of casein to the eluted TRF to obtain a protein having DNA binding activity.

8. A method for purifying telomerase from mammalian cells comprising:
   a) isolating nuclei from tissue culture cells;
   b) preparing restriction fragments from the nuclear extracts of the nuclei;
   c) contacting the nuclear extracts with an affinity chromatography column comprising bound TRF; and
   d) eluting telomerase from the column.

9. A human TRF having an amino acid sequence substantially homologous to that of SEQ ID NO:12.

10. An active fragment of a vertebrate telomere repeat binding factor TRF), having an amino acid sequence substantially homologous to that of SEQ ID NO:12; wherein said fragment binds TTAGGG repeats but not TTGGGG or TTAGGC repeats; and
    wherein said vertebrate TRF has the following characteristics:
    a) it binds to telomere repeat sequences when it is not in a highly purified form;
    b) it does not bind DNA when it is highly purified, but its DNA binding activity can be rescued in the presence of casein; and
    c) it is a member of the Myb family of DNA binding proteins.

11. The active fragment of claim 10 wherein the vertebrate TRF protein is a mammalian TRF protein.

12. The active fragment of claim 11 which comprises an Myb type binding domain with an amino acid sequence of SEQ ID NO:15.

13. An active fragment of claim 9 wherein the TRF protein has the amino acid sequence of SEQ ID NO:12.

14. The active fragment of claim 13 containing a detectable label.

15. A proteolytic fragment of a vertebrate TRF, having an amino acid sequence substantially homologous to that of SEQ ID NO:12; wherein said vertebrate TRF has the following characteristics:
    a) it binds to telomere repeat sequences when it is not in a highly purified form;
    b) it does not bind DNA when it is highly purified, but its DNA binding activity can be rescued in the presence of casein; and
    c) it is a member of the Myb family of DNA binding proteins.

16. The proteolytic fragment of claim 15, wherein said proteolytic fragment is produced by pepsin digestion of the vertebrate TRF.

17. The proteolytic fragment of claim 15 wherein the vertebrate TRF protein is a mammalian TRF protein.

18. A proteolytic fragment of claim 9 wherein the TRF protein has the amino acid sequence of SEQ ID NO:12.

19. A proteolytic fragment of claim 18 containing a detectable label.

* * * * *